United States Patent
Audoin et al.

(10) Patent No.: US 10,578,555 B2
(45) Date of Patent: Mar. 3, 2020

(54) ACOUSTIC RESONANCE SPECTROMETRY SYSTEM AND METHOD

(71) Applicants: UNIVERSITE DE BORDEAUX, Bordeaux (FR); INSTITUT POLYTECHNIQUE DE BORDEAUX, Talence (FR); CENTRE NATIONALE DE LA RECHERCHE SCIENTIFIQUE, Paris (FR); ECOLE NATIONALE SUPERIEURE DES ARTS ET METIERS, Paris (FR); COMMISSARIAT A L'ENERGIE ATOMIQUE ET AUX ENERGIES ALTERNATIVES, Paris (FR); INSTITUT D'OPTIQUE GRADUATE SCHOOL, Palaiseau (FR)

(72) Inventors: Bertrand Audoin, Pessac (FR); Eric Cormier, Cestas (FR); Jérôme Lhermite, Anglet (FR); Giorgio Santarelli, Talence (FR); Yannick Guillet, Villenave d'Ornon (FR); Adrien Aubourg, Bordeaux (FR)

(73) Assignees: UNIVERSITE DE BORDEAUX, Bordeaux (FR); INSTITUT POLYTECHNIQUE DE BORDEAUX, Talence (FR); CENTRE NATIONALE DE LA RECHERCHE SCIENTIFIQUE, Paris (FR); ECOLE NATIONALE SUPERIEURE DES ARTS ET METIERS, Paris (FR); COMMISSARIAT A L'ENERGIE ATOMIQUE ET AUX ENERGIES ALTERNATIVES, Paris (FR); INSTITUT D'OPTIQUE GRADUATE SCHOOl, Palaiseau (FR)

( * ) Notice: Subject to any disclaimer, the term of this patent is extended or adjusted under 35 U.S.C. 154(b) by 0 days.

(21) Appl. No.: 16/318,845

(22) PCT Filed: Jul. 19, 2017

(86) PCT No.: PCT/FR2017/051973
§ 371 (c)(1),
(2) Date: Jan. 18, 2019

(87) PCT Pub. No.: WO2018/015663
PCT Pub. Date: Jan. 25, 2018

(65) Prior Publication Data
US 2019/0242820 A1    Aug. 8, 2019

(30) Foreign Application Priority Data

Jul. 20, 2016  (FR) ..................................... 16 56926

(51) Int. Cl.
*G01J 3/00* (2006.01)
*G01N 21/63* (2006.01)
(Continued)

(52) U.S. Cl.
CPC .......... *G01N 21/636* (2013.01); *G01J 3/4412* (2013.01); *G01J 2009/006* (2013.01); *G01N 2021/638* (2013.01)

(58) Field of Classification Search
CPC ............ G01N 21/636; G01N 2021/638; G01J 3/4412; G01J 2009/006
See application file for complete search history.

(56) References Cited

U.S. PATENT DOCUMENTS 4,710,030 A * 12/1987 Tauc .................. G01N 21/1702
356/432
5,615,675 A * 4/1997 O'Donnell ......... G01N 29/0681
600/425

(Continued)

OTHER PUBLICATIONS

International Search Report, PCT/FR2017/051973, dated Oct. 9, 2017.

(Continued)

*Primary Examiner* — Tarifur R Chowdhury
*Assistant Examiner* — Jonathon Cook
(74) *Attorney, Agent, or Firm* — Young & Thompson (57) ABSTRACT

Disclosed is an acoustic resonance spectrometry system for analysing a sample, which includes an optical pump-probe device adapted to generate a pump beam and a probe beam, the pump beam being consisted of a series of ultra-short pump light pulses having a repetition frequency in the (Continued)

spectral domain of the gigahertz, the pump beam being directed towards an optoacoustic transducer to generate a periodic grating of coherent acoustic phonons in the sample, the probe beam being directed towards the sample to form a scattering beam of the probe beam on the grating of phonons, a frequency variation device being adapted to vary the repetition frequency of the pump beam in a spectral range and a photo-detection system configured to measure a scattering signal as a function of the repetition frequency in the spectral range.

20 Claims, 3 Drawing Sheets

(51) Int. Cl.
    *G01J 3/44*      (2006.01)
    *G01J 9/00*      (2006.01)

(56) References Cited

U.S. PATENT DOCUMENTS

2006/0272419 A1* 12/2006 Maris ............... A61B 5/0097
                                                                                73/606
2014/0240710 A1* 8/2014 Shigekawa ........ G01N 21/1717
                                                                                356/445

OTHER PUBLICATIONS

Fernando Perez-Cota et al: "Thin-film optoacoustic transducers for subcellular Brillouin oscillation imaging of individual biological cells", Appli ed Opti cs, vol. 54, No. 28, Sep. 28, 2015 (Sep. 28, 2015), p. 8388, XP055362715, Washington, DC; US ISSN: 0003-6935, 001: 10.1364/AO.54.008388.

Smith Richard J et al: "Optically excited nanoscale ultrasonic transducers", The Journal of the Acoustical Society of America, American Institute of Physics for the Acoustical Society of America, New York, NY, US, vol. 137, No. 1, Jan. 1, 1901 (Jan. 1, 1901), pp. 219-227, XP012193881, ISSN: 0001-4966, 001: 10.1121/1.4904487 [retrieved on Jan. 1, 1901].

Maznev A A et al: "Coherent Brillouin spectroscopy in a strongly scattering liquid by picosecond ultrasonics", Optics Letters, Optical Society of America, vol. 36, No. 15, Aug. 1, 2011 (Aug. 1, 2011), pp. 2925-2927, XP001569589, ISSN: 0146-9592, 001: 10.1364/0L.36.002925 [retrieved on Aug. 1, 2011].

Quantum Laser: "Ultrafast optical sampling oscilloscope", May 3, 2016 (May 3, 2016), XP055362452, Retrieved from the Internet: URL:http://www.laserquantum.com/blog/ultra fast-optical-sampling-oscilloscope/#sthashLOUDVFw3h.dpbs [retrieved on Apr. 6, 2017] the whole document.

Stashkevich et al., "High-intensity Brillouin light scattering by spin waves in a permalloy film under microwave resonance pumping"., Citation: Journal of Applied Physics 102, 103905 (2007); doi: 10.1063/1.2815673.

Maris., :Picosecond Ultrasonics., "Brief pulses of high-frequency sound allow experimenters to probe connections inside a computer chip" Scientific American Jan. 1998.

Dehoux et al., "All-Optic Broadband Ultrasonography of Single Cells"., Scientific Report,, 5:8650, DOI: 10.1038/srep08650.

Scarcelli et al., "Confocal Brillouin Microscopy for Three-Dimensional Mechanical Imaging"., Nat Photonics. Dec. 9, 2007; 2: 39-43. doi: 10.1038/ nphoton. 2007.250.

Lin et al., "Phonon attenuation and velocity measurements in transparent materials by picoseconds acoustic interferometry"., J. Appl. Phys. 69 (7), Apr. 1, 1991.

* cited by examiner

ACOUSTIC RESONANCE SPECTROMETRY SYSTEM AND METHOD

TECHNICAL FIELD TO WHICH THE INVENTION RELATES

The present invention generally relates to the field of devices for measuring mechanical properties of a sample at the microscopic or nanoscopic scale.

More particularly, it relates to a Brillouin scattering measurement system and method for the non-destructive analysis of a sample. More precisely, it relates to a measurement of the optoacoustic type induced and detected by a light beam.

TECHNOLOGICAL BACKGROUND

Different techniques exist for measuring mechanical properties of elasticity of thin-film materials.

Thin-film elasticity measurements are commonly performed by indentation. Indentation consists in applying a determined load at the surface of a material then measuring the indent induced by the deformation of the material. Indentation is, by nature, destructive. Moreover, indentation involves simultaneously the elastic properties of compression and shearing, as well as the plasticity of the material. The quantitative analysis of the indent is hence complex. Finally, indentation does not allow quantifying the adhesion of a material.

The spontaneous Brillouin scattering technique is based on the inelastic scattering of an incident continuous light beam by incoherent phonons of thermal origin naturally present within the medium to be analysed. The scattered optical signal contains the information about the phonon velocity, which gives access to the elasticity of the medium and in particular to the anisotropic elasticity. The spontaneous Brillouin scattering technique has been applied in very numerous fields. However, the very low level of the Brillouin scattering signal generally requires a significant interaction volume. To overcome this limit, the publication of A. A. Stashkevich, P. Djemia, Y. K. Fetisov, N. Bizière and C. Fermon, "High-Intensity Brillouin light scattering by spin waves in a permalloy film under microwave resonance pumping", J. Appl. Phys. 102, 103905, 2007, proposes an amplification of the signal from an external microwave source. Moreover, the use of phase-grating spectrometers has allowed increasing the sensitivity of detection of the Brillouin scattering photons. The publication of G. Scarcelli and S. H. Yun, "Confocal Brillouin microscopy for three-dimensional mechanical imaging", Nat. Photonics 2, 39-43, 2008, illustrates experiments of confocal Brillouin microscopy for imaging mediums, in particular biological mediums. However, the very low amplitude of the incoherent thermal phonons requires, on the one hand, degrading the spatial resolution of the images and needs, on the other hand, a point-by-point acquisition, which makes impossible the real-time image acquisition.

The measurement technique based on the spontaneous Brillouin scattering is very little used outside laboratories. This technique is incompatible with the full-field imaging and does not allow deducing therefrom measurements of adhesion between materials.

In microelectronics, the metrology of the thin layer elasticity properties is performed by a picosecond acoustics technique. Picosecond acoustics is a time-resolved pump-probe technique that uses a pump light beam comprising one or several laser pulses for generating coherent acoustic phonons and a timely-offset probe light beam with an adjustable delay with respect to the pump beam for detecting the Brillouin scattering on the coherent phonons in a spectral range from GHz to THz. The pump laser pulses are ultra-short laser pulses. In the present document, it is meant by ultra-short pulse a pulse whose duration is comprised between about ten femtoseconds and about hundred picoseconds. The pump light beam and the probe light beam may come from a same source or from two distinct sources. The pump and probe light beams may have the same wavelength or different wavelengths.

Figure 1:
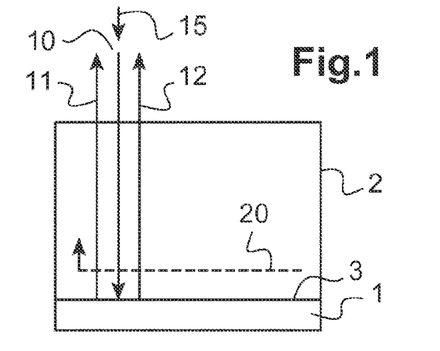
FIG. 1 schematically shows the principle of a picosecond acoustic measurement according to the prior art.

FIG. 1 schematically shows a picosecond acoustic device and method according to the prior art. A sample 2 to be analysed has an interface 3 with an optoacoustic transducer 1. By way of example, the optoacoustic transducer 1 is metallic or includes a thin-film metallic coating. The sample may be deposited or fastened, for example by bonding, on the optoacoustic transducer 1. A pump light beam, or pump beam, 10 consisted of a single laser pulse of sub-picosecond duration is considered. The single-pulse pump light beam 10 is incident on the sample 2 to be analysed and transmitted towards the interface 3. The partial absorption of the pump laser pulse by the transducer material 1 generates, by optoacoustic conversion, an acoustic front 20 that propagates in the sample 2 in the opposite direction of the incident laser pulse. This acoustic front 20 generates a transitory deformation field that induces disturbances of the refractive index of the sample. A probe light beam, or probe beam, 15 is directed towards the sample. In the example of FIG. 1, the pump beam and the probe beam are in normal incidence on the sample. The probe beam 15 is timely offset with respect to the pump beam 10. A portion 11 of the probe beam that is not absorbed is reflected at the interface 3 between the optoacoustic transducer 1 and the sample 2. Another portion 12 of the probe beam is back-scattered due to the Brillouin interaction on the acoustic wave front 20. The reflected beam and the back-scattered beam interfere with each other and create temporal modulations or oscillations. The frequency of these interferences is linked to the velocity of the coherent phonons in the sample. The reflected beam and the back-scattered beam are collected. The detection of the time trace of the relative change of reflectivity of the probe beam allows measuring the disturbances of the refractive index of the sample. For a sample consisted of a propagation medium transparent enough to the pump beam and to the probe beam, the picosecond acoustics technique allows detecting in the time domain Brillouin oscillations that give access to the velocity of the acoustic waves. An advantage of this technique comes from the fact that the amplitude of the Brillouin scattering signal generated by the conventional picosecond acoustics technique, i.e. by coherent phonons, is higher than when this diffusion is initiated by thermal phonons.

However, in a conventional picosecond acoustics experiment, the pulse excitation generates a wideband spectrum of coherent phonons extending up to the terahertz (THz). Only the spectral component of the transitory acoustic signal in tune with the Brillouin frequency then contributes to the photo-elastic interaction. The detection of the coherent phonons by picosecond acoustics hence requires the use of a synchronous detection system. Now, to our knowledge, there exists no imaging system based, for example, on a CCD camera, having a synchronous detection on each pixel of the camera, so that full-field detection on a CCD camera is not possible in picosecond acoustics.

The developments of the picosecond acoustics technique have been initiated by researches in solid state physics and the main industrial applications are found in the field of microelectronics. First applications of the picosecond acoustics technique to biology have allowed access to the mechanical properties of a biological cell at a sub-cell scale, represented as an image.

The picosecond acoustics technique can also be applied to non-transparent thin layers. It may give access to thickness measurements. The very low signal-to-noise ratio makes it necessary to use a synchronous detection. However, the acquisition times are long, not easily compatible with imagery.

During measurements of Brillouin lines by the conventional picosecond acoustics technique, the spectral resolution is limited by the repetition frequency of the pulse laser, generally of the order of 80 MHz or 50 MHz.

The document H. J. Maris "Picosecond ultrasonics" Sci. Am. 278, 64-67, 1998, describes a measurement device based on the emission of a picosecond laser pulse incident on a multi-layer sample to be analysed. A first picosecond laser pulse, called pump pulse, heats the sample and induces an acoustic pulse propagating in the multi-layer sample. This acoustic pulse is transmitted through the different layers towards the surface of the sample and modifies the optical properties of the surface. A second picosecond laser pulse, called probe pulse, is directed to the sample. By comparing the temporal shape of the optical wave reflected on the surface with that of the probe pulse emitted, the instant at which the echo of the acoustic wave reaches a peak can be determined, with a sub-picosecond resolution. The picosecond ultrasonics technique hence allows non-destructively measuring the thicknesses and the interfaces of a multi-layer sample with accuracy lower than one Angstrom.

The publication H. N. Lin, R. J. Stoner, H. J. Maris and J. Tauc, "Phonon attenuation and velocity measurement in transparent materials by picosecond acoustic interferometry, J. Appl. Phys., 69, 3816, 1991", describes another technique of picosecond acoustic interferometry, in which a picosecond pump pulse is transmitted through a sample to be analysed then absorbed on an interface with a metal film. This absorption generates coherent acoustic phonons that propagate in the sample and induce a local modification of the optical index. A picosecond probe pulse, timely offset with respect to the pump pulse, is directed to the sample. The probe pulse creates multiple scatterings and reflections between the phonons and the interface with the metal film. The measurement of the variations of optical reflectivity on the sample as a function of time makes appear oscillations due to the interferences between the multiple scatterings and reflections. The analysis of these picosecond acoustic interferometry measurements as a function of time allows deducing therefrom the velocity of the phonons.

The publication G. Scarcelli and S. H. Yun, "Confocal Brillouin microscopy for three-dimensional mechanical imaging", Nat. Photonics 2, 39-43, 2008, describes a confocal microscopy device based on a continuous laser source and a Brillouin scattering spectrometer to form two- or three-dimensional (2D or 3D) optical microscopy images, revealing the mechanical properties of a biological cell in solution. However, the intensity of the Brillouin scattering spectra is generally very low.

The publication A. A. Stashkevich, P. Djemia, Y. K. Fetisov, N. Bizière and C. Fermon, "High-Intensity Brillouin light scattering by spin waves in a permalloy film under microwave resonance pumping", J. Appl. Phys. 102, 103905, 2007, describes a Brillouin scattering measuring device assisted by a microwave excitation. This coupling of a light excitation source and a microwave excitation makes it possible, according to the authors, to increase the Brillouin scattering measurement by three orders of magnitude when there is a resonance with spin waves.

The publication T. Dehoux, M. Abi Ghanem, O. F. Zouani, J.-M. Rampnoux, Y. Guillet, S. Dilhaire, M.-C. Durrieu and B. Audoin, "All-optical broadband ultrasonography of single cells", Scientific Reports, 5:8650, DOI 10.1038, 2015, describes an optoacoustic pulse inverted microscope comprising a first and a second picosecond pulse laser, a photodiode detector and an optoacoustic transducer consisted of a sapphire substrate having an interface with a titanium film. The first laser emits pump laser pulses at a first wavelength and a first repetition frequency towards the sapphire substrate of the optoacoustic transducer, the other interface of the titanium film being in contact with a single-cell to be analysed. Each pump laser pulse is absorbed into the titanium film and generates an acoustic pulse, which is reflected on the titanium-cell interface. The second laser emits probe pulses at another wavelength and another repetition frequency. The probe pulses are focused to the titanium-sapphire interface, hence allowing detecting the mechanical properties of the observed cell. The photodiode acquires, as a function of time, the optical reflectivity variations by elasto-optical coupling on the titanium-sapphire interface. This optoacoustic pulse inverted microscope allows studying the adhesion of a single cell to a titanium film. In this system, no laser pulse reaches the titanium-cell interface. The drawback of this system is that the acquisition, made point-by-point, is long.

It is desirable to have at one's disposal a fast analysis of the acoustic properties of inhomogeneous materials, thin layers or biological cells, which is two dimensionally-, or possibly 3D-, resolved over distances of several hundreds of nanometres to several microns, while having an increased sensitivity.

OBJECT OF THE INVENTION

In order to remedy the above-mentioned drawbacks of the state of the art, the present invention proposes a system for Brillouin scattering measurement by acoustic resonance spectrometry for analysing the mechanical properties of a sample.

More particularly, it is proposed according to the invention an acoustic resonance spectrometry system comprising:
- an optoacoustic transduction means having an interface in contact with a sample to be analysed,
- an optical pump-probe device adapted to generate a pump beam and a probe beam, the pump beam being consisted by a series of ultrashort pump light pulses having a repetition frequency located in a spectral domain comprised between several hundreds of megahertz and several tens of gigahertz, and a pump wavelength adapted to the transparency of the material of the sample, and
- optomechanical means for directing the pump beam towards the optoacoustic transduction means and for generating, by optoacoustic conversion, a periodic spatial grating of coherent acoustic phonons in the sample, the periodic spatial grating of phonons having a pitch determined as a function ratio between the repetition frequency of the pump beam and an acoustic velocity of the phonons in the sample, the probe beam having a probe wavelength adapted to the transparency of the material of the sample, and
- other optomechanical means for directing the probe beam towards the sample so as to form a scattering beam of the probe beam on the periodic grating of phonons, a frequency variation device adapted to vary the repetition frequency F of the pump beam in a spectral range, so as to vary the pitch P of the periodic grating of phonons in the sample, and a photo-detection system configured to receive the scattering beam and to measure a scattering signal as a function of the repetition frequency.

Advantageously, the repetition frequency of the pump beam is comprised in a range extending between a few hundreds of megahertz and a few tens of gigahertz, for example between 0.5 GHz and 50 GHz, and preferably between 4 GHz and 20 GHz.

Advantageously, a signal processing system is configured to process the detected scattering signal as a function of the variable repetition frequency F and to extract therefrom a resonance frequency $f_B$ corresponding to a Brillouin scattering amplified by resonance on the grating of phonons.

This acoustic spectrometry system hence allows a resonant Brillouin scattering measurement when the pitch (P) of the periodic grating of phonons is equal to an integral multiple of the half-wavelength of the probe beam, for a probe beam in normal incidence.

Without being bound by theory, when the repetition frequency of the pump pulses reaches the Brillouin resonance, the probe beam is more efficiently reflected on the sample, which corresponds to the Bragg conditions for the probe beam. The Brillouin scattering measurement system is based on the Brillouin interaction between a sample and a train of picosecond pump laser pulses having a high repetition frequency, in the gigahertz domain, i.e. in the Brillouin scattering frequency domain for most of the materials. Moreover, this repetition frequency is tunable for example in a spectral range also located in the gigahertz domain. For example, the variations of the repetition frequency extend over a spectral range comprised between 5 and 20 GHz. In a given application, the scanning of the repetition frequency may be limited to a more limited spectral range, for example near a pre-evaluated Brillouin scattering frequency, for example, in the example illustrated in FIG. 12, between 16.4 GHz and 17.1 GHz.

The interaction between the pump beam and the sample allows generating a periodic grating of coherent acoustic phonons maintained at the repetition frequency of the pump beam. The Brillouin resonance frequency of the material may be detected directly in a signal formed by scattering of the probe beam to the grating of phonons, this signal being measured as a function of a scanning of the repetition frequency of the pump beam.

The detected signal resulting from the scattering on the periodic grating of phonons is hence amplified by resonance at the Brillouin frequency. The high amplitude of this resonant Brillouin scattering signal makes it possible to form an image of the sample by means of a real-time full-field optical imaging system.

Other non-limitative and advantageous features of the frequency-resolved acoustic resonance spectrometry system according to the invention, taken individually or according to all the technically possible combinations, are the following:

the optical pump-probe device comprises a laser configured to emit a monochromatic continuous laser beam, a variable frequency microwave generator configured to generate a control signal at said repetition frequency and a plurality of electro-optical modulators configured to receive the control signal and to modulate the monochromatic continuous laser beam in amplitude and in phase at said repetition frequency and a compressor configured to receive the laser beam modulated in amplitude and in phase at said repetition frequency to generate the pump beam, this pump beam having an optical comb-like spectral distribution comprising a plurality of discrete wavelengths separated by a free spectral interval determined by the repetition frequency;

the probe beam in temporally continuous;

the probe beam is consisted of another series of ultra-short probe light pulses;

the pump beam having a pump wavelength, the probe wavelength is different from the pump wavelength, or, according to an alternative embodiment, the probe wavelength is equal to the pump wavelength.

In a particular embodiment, a single laser source is used to generate the pump beam and the probe beam, the probe beam being consisted of a portion of the pump beam.

According to other particular and advantageous aspects of the acoustic resonance spectrometry system:

the optomechanical means are configured so that the pump beam and the probe beam are in normal incidence on the sample; according to an alternative embodiment, the pump beam is in normal incidence on the sample and the probe beam in oblique incidence on the sample, or, according to another alternative embodiment, the pump beam is in oblique incidence on the sample and the probe beam in normal incidence on the sample, or, according to still another alternative embodiment, the pump beam is in oblique incidence on the sample and the probe beam is in another oblique incidence on the sample;

the frequency variation device is adapted to vary the repetition frequency of the pump beam in the spectral range comprised between 0.5 GHz and 20 GHz, and preferably between 5 GHz and 20 GHz, continuously, or with a pitch of a few hertz or a few kHz;

the probe beam is configured to illuminate an area of the sample and the photo-detection system includes a two dimensionally-resolved image detector and an optical image forming system configured to form an image of said sample area on the image detector, the photo-detection device having preferably a micrometre or sub-micrometre spatial resolution of the sample.

Advantageously, the system for resonant Brillouin scattering measurement by frequency-resolved acoustic spectrometry includes a signal processing system adapted to analyse the acoustic scattering signal as a function of the repetition frequency and to deduce therefrom a resonant Brillouin scattering frequency when the repetition frequency of the pump beam is such that the pitch of the periodic grating of phonons is equal to an integral multiple of a half-wavelength of the probe beam. Advantageously, the signal processing system is adapted to calculate at least one value of mechanical property of the sample analysed as a function of the resonant Brillouin scattering frequency.

The invention also proposes an acoustic resonance spectrometry method, the method comprising the following steps:

generating a pump beam consisted by a series of ultra-short pump light pulses having a repetition frequency located in a spectral domain comprised between several hundreds of megahertz and several tens of gigahertz;

the pump beam being incident, preferably by transmission through a sample to be analysed, on an optoacoustic transduction means having an interface with a sample to be analysed, so as to generate a periodic grating of coherent acoustic phonons in the sample, the periodic grating of phonons having a pitch determined as a function of a ratio between the repetition frequency of the pump beam and an acoustic velocity of the coherent acoustic phonons in the sample;

generating a probe beam having a probe wavelength, the probe beam being directed towards the sample so as to form a beam scattered by scattering of the probe beam on the periodic grating of coherent acoustic phonons;

varying the repetition frequency of the pump beam in a spectral range so as to vary the pitch of the periodic grating of coherent acoustic phonons in the sample;

photo-detecting the scattered beam as a function of the variable repetition frequency in said spectral range, and measuring a scattering signal as a function of the repetition frequency in said spectral range.

Advantageously, a processing of the scattering signal as a function of the repetition frequency allows deducing therefrom a resonant Brillouin scattering measurement when the repetition frequency is such that the pitch of the periodic grating of phonons is equal to an integral multiple of a half-wavelength of the probe beam.

This system and method for resonant Brillouin scattering measurement by frequency-resolved acoustic spectrometry finds applications in particular in the characterization of materials and in bio-photonics.

DETAILED DESCRIPTION OF AN EXEMPLARY EMBODIMENT

The following description with respect to the appended drawings, given by way of non-limitative examples, will permit a good understanding of what the invention consists in and of how it can be implemented.

The present disclosure relates to an acoustic resonance spectrometry technique based on an optical pump-probe technique, where the acoustic frequency may be scanned in continuous by varying the repetition frequency of the pulses of the pump beam so as to determine the Bragg condition for the Brillouin scattering of the probe beam. The system then acts as an acoustic monochromator. This frequency-resolved acoustic spectrometry technique allows increasing the efficiency of detection of the Brillouin scattering.

The limits related to the conventional picosecond acoustics technique are overcome in the present disclosure thanks to a frequency analysis that implements a repetition frequency scanning in combination with an acoustic frequency resolution of a few kHz for an accurate measurement of Brillouin scattering at resonance.

Device

In order to explain the operation of the system, a sample 2 to be analysed, deposited on or placed in contact with an optoacoustic transducer 1, is considered. The interface 3 between the optoacoustic transducer 1 and the sample 2 is preferably planar.

Figure 2:
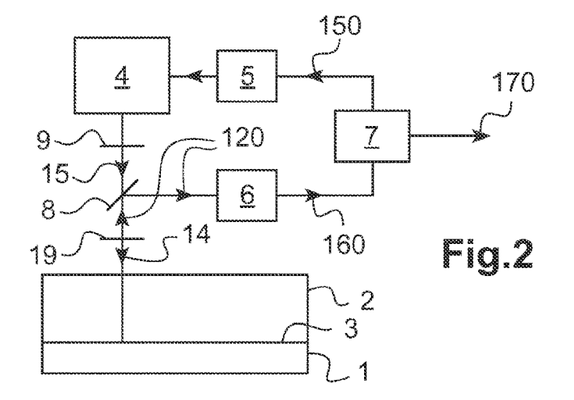
FIG. 2 schematically shows an acoustic resonance spectrometry system according to a first embodiment of the invention.

In FIG. 2 is shown an acoustic resonance spectrometry system according to a first embodiment of the invention. In this first embodiment, a single and same source of ultra-short laser pulses is used to form the pump beam 14 and the probe beam 15. As described in detail hereinafter, the pump beam 14 generates a periodic spatial grating of coherent acoustic phonons in the sample. The probe beam 15 allows generating a back-scattered beam by Brillouin interaction of the probe beam 15 on this periodic grating of coherent acoustic phonons.

The system of FIG. 2 includes a light source device 4, a frequency variation device 5, a detection system 6 and a control and signal processing unit 7. In the example illustrated in FIG. 2, the system further includes a half-wave plate 9, a polarization splitting cube 8 and a quarter-wave plate 19. The support is arranged so that the incident radiation is preferably in normal incidence on the sample 2 and/or on the interface 3 between the sample 2 and the optoacoustic transducer 1. The light source device 4 generates an ultra-short laser pulse train at a repetition frequency F.

In the present document, it is understood by laser pulse train, or, equivalently, series of laser pulses, a temporal series of laser pulses, in which each pulse is emitted at an instant temporally separated by 1/F from the following and/or preceding pulse, where F represents the repetition frequency of the pulse train. Advantageously, the laser pulses of a same pulse train have all the same spectral and temporal properties.

At the exit of the light source device 4, the laser pulses are for example linearly polarized. The half-wave plate 9 is preferably arranged at 45 degrees, on the one hand, from the linear polarization axis of the source pulses and, on the other hand, from the axes of the polarization splitting cube 8. The quarter-wave plate 19 is passed through a first time, on the outward way, by the incident light pulses of the pump beam 14 or of the probe beam 15. The quarter-wave plate 19 is passed through another time by a light beam formed by reflection and scattering of the probe beam 15 on the sample 2. In total, the quarter-wave plate 19 hence introduces a delay equal to that of a half-wave plate. Consequently, at the polarization splitting cube 8, the reflection and/or scattering light beam 120 is polarized perpendicularly with respect to the pump beam 14 and to the probe beam 15. Hence, the polarization splitting cube 8 allows separating the reflection and scattering light beam 120 to direct it towards the detection system 6.

The detection system 6 detects the reflection and scattering light beam 120 and forms an electronic signal 160. The unit 7 controls the repetition frequency variation device 5 so as to vary the repetition frequency F of the pulse train emitted by the light source device 4. The light source device 4 generates a pump beam 14 consisted of pulses having a repetition frequency F located in a spectral domain of the order of the gigahertz. By way of non-limitative example, the spectral domain of the repetition frequency is located between 0.5 GHz and 40 GHz. Moreover, the repetition frequency variation device 5 scans the repetition frequency F in a frequency range, or a spectral range, also located in the gigahertz domain. The scanning of the frequency F may be continuous or by steps of a few hertz to a few kHz in a spectral range. The unit 7 allows processing the detected reflection and scattering signal as a function of the repetition frequency F of the pulses of the pump beam 14 to extract therefrom a Brillouin scattering signal measurement. This Brillouin scattering signal is resonant when the pitch P of the phonon grating is equal to a half-wavelength of the probe beam 15.

The variable-frequency light source device 4 preferably comprises a source of the optical frequency comb type having a repetition frequency F that is simply tunable in a spectral range from 0.5 to 40 GHz and, preferably, from 1 to 20 GHz, or from 5 to 11 GHz.

Presently, there mainly exist two optical frequency comb generation techniques. A known technique lies on the use of a laser cavity whose operation in pulse mode is obtained by mode locking. Such a laser cavity allows generating laser pulses of picosecond to femtosecond duration, with a repetition frequency of the order of 10 MHz to 1 GHz, defining an optical frequency comb whose free spectral interval is determined by the length of the cavity. By changing the cavity length, it is possible to vary the repetition frequency. However, the repetition frequency scanning is then limited to a limited spectral range, due to the instabilities in the cavity.

Figure 3:
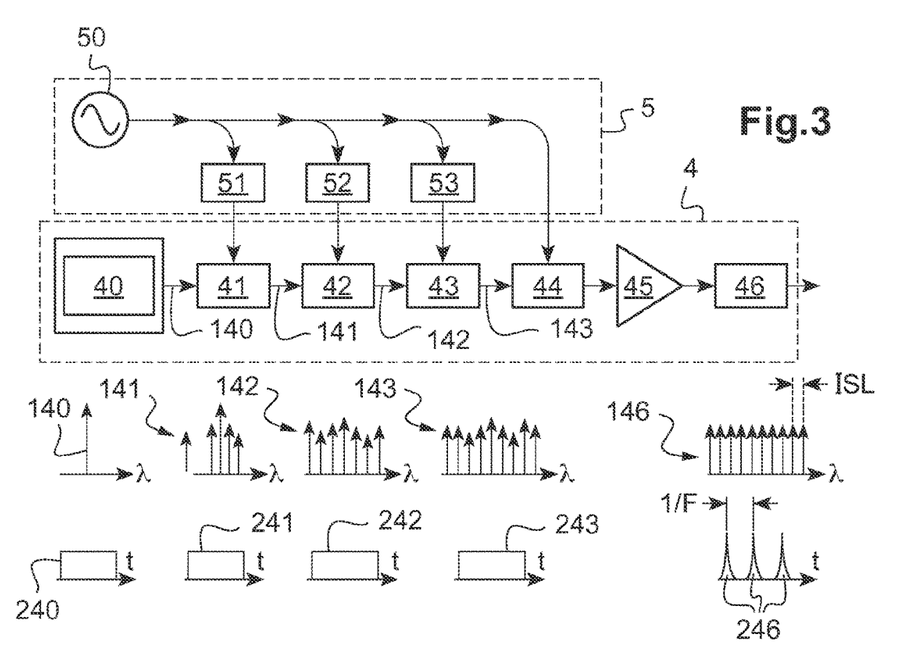
FIG. 3 schematically illustrates the structure and operation of a pulse source of the optical comb type.

In the present disclosure, a technique schematically illustrated in FIG. 3 is preferably used to generate the pump beam 14. Herein, the light source device 4 includes a single-frequency continuous laser source 40 and electro-optical modulators 41, 42, 43, 44 to generate an optical frequency comb. In certain embodiments, the same light source device 4 also generates the probe beam 15.

FIG. 3 schematically shows an example of architecture proposed for a variable repetition frequency light pulse generation system. This device includes a laser diode 40, optical modulators 41, 42, 43, 44, an optical amplifier system 45 and a compressor 46. The wavelength spectrum and the temporal shape of the output light radiation of the laser diode 40, the different optical modulator and the compressor 46, respectively, are also schematically shown in FIG. 3.

The laser diode 40 is preferably a fibered laser diode that emits a temporally continuous laser radiation 140. By way of non-limitative example, the laser radiation 140 is emitted at a wavelength of 1030 nm. At the exit of the laser diode 40, three phase modulators 41, 42, 43 are arranged in series. The phase modulator 41, 42, 43 are controlled by a same low-noise microwave generator 50. More precisely, the microwave generator 50 modulates the modulation voltage 51, respectively 52, 53, of each phase modulator 41, respectively 42, 43. The microwave generator 50 has a modulation frequency F located in the spectral range of the gigahertz, for example of the order of 0.5 to 20 GHz, or even 40 GHz.

Hence, the phase modulator 41 introduces a phase-shift PHI1. At the exit of the phase modulator 41, the laser radiation is temporally continuous and has a plurality of discrete wavelengths shown on the spectrum 141. Similarly, each phase modulator 42, respectively 43, introduces an additional phase-shift PHI2, respectively PHI3. The three modulation voltages 51, 52, 53 are carefully adjusted so as to generate a temporally continuous laser radiation (see the temporal shapes 241, respectively 242, 243) with a comb of discrete wavelengths, as shown on the spectrum 141, respectively 142, 143. A fourth amplitude modulator 44 is arranged at the exit of the phase modulators and completes the modulation device. The microwave generator 50 modulates the modulation voltage of the amplitude modulator 44. The amplitude modulator 44 modulates the amplitude of the radiation at the modulation frequency of the generator 50. The output laser radiation of the optical modulators 41 to 44 is then amplified by an optical amplifier system 45, then temporally compressed by a compressor 46. Preferably, the optical amplifier system 45 and/or the compressor are based on optical fibre components. The optical amplifier system 45 comprises for example one or several Ytterbium-doped-fibre amplifiers arranged in series. A compressor 46 is arranged at the exit of the optical amplifier system 45. The compressor 46 allows compensating for the phase-shifts induced by the modulators 41 to 44 so as to compress the duration of the emitted pulses 14 up to one picosecond or even a few hundreds of femtoseconds. At the exit of the source device 4, the temporal shape 246 of the radiation is no longer continuous but modulated to the repetition frequency F.

Advantageously, the microwave generator 50 applies to the phase modulators 41, 42, 43 and, respectively, to the amplitude modulator 45, a phase and, respectively, amplitude modulation, in a spectral domain of microwave frequencies able to go from 0.5 to 20 GHz. The light source device 4 hence allows producing a train of ultra-short pulses 246 having a repetition frequency F equal to the modulation frequency of the microwave generator located in the spectral domain of the gigahertz.

Moreover, the repetition frequency F is adjustable by adjustment of the frequency of the microwave generator 50. The repetition frequency F is hence located in the spectral domain of the gigahertz and adjustable in a spectral range able to go, for example, from 5 GHz to 20 GHz. That way, the repetition frequency of the ultra-short laser pulses 246 is easily adjustable by modification of the frequency of the microwave generator 50.

The train of ultra-short pulses 246 shows spectrally an optical frequency comb 146, in other words a comb of discrete wavelengths, separated by a free spectral interval or ISL determined by the modulation frequency of the signal controlling the modulators 41, 42, 43, 44. Indeed, the multiple modulations produce lateral lines 141, 142, 143, around the optical frequency 140 of the continuous laser. By way of example, the wavelength comb extends spectrally over about 3 nm around the wavelength of 1030 nm.

The technology of ytterbium-doped-fibre laser source 40, having a central emission line at about 1030 nm, is perfectly adapted to the efficient amplification, by means of an optical amplifier 45, up to very high mean power levels, for example higher than 100 W. On the one hand, such an optical-fibre laser source allows adjusting easily the repetition frequency F of the pulses 246. On the other hand, such an optical-fibre laser source allows generating a high power laser.

A light source device generating a train of light pulses 246 at a very high repetition frequency, adjustable in a spectral range, is hence available. In the temporal domain, these ultra-short light pulses 246 have an ultra-short duration and a repetition frequency F continuously or discretely adjustable in a spectral range of the order of the gigahertz. In the spectral range, these ultra-short light pulses 14 form a comb of discrete, periodic optical frequencies, separated by a free spectral interval ISL determined by the repetition frequency F.

The use of this pulse train adjustable in repetition frequency F for an acoustic spectrometry measurement, applied to the Brillouin scattering measurement, will now be described. According to a first embodiment, the same source device generates the pump beam 14 and the probe beam 15. In this case, the pump beam 14 and the probe beam 15 are consisted of ultra-short pulses at the same repetition frequency F.

Figure 4:
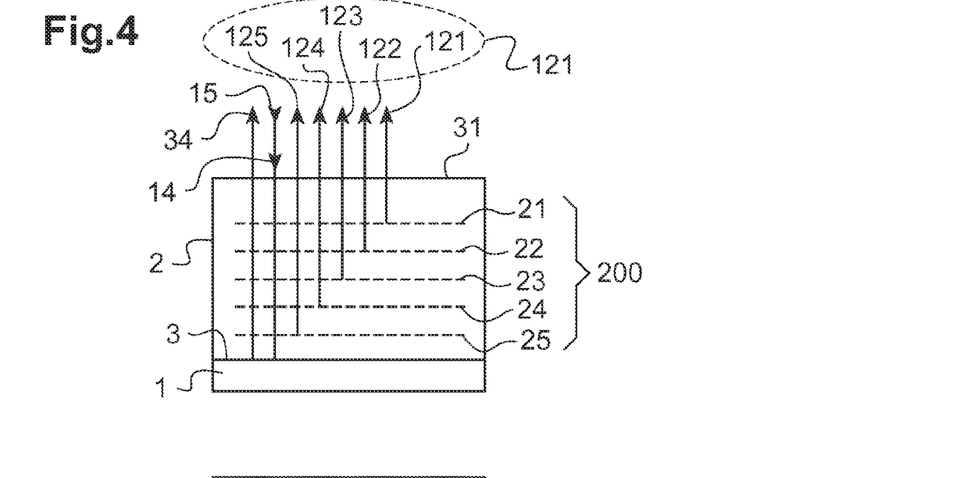
FIG. 4 illustrates a configuration for the resonant Brillouin scattering measurement according to a first embodiment of the invention.

In FIG. 4 is shown a sample 2 to be analysed. The sample has an interface 3 with optoacoustic transducer 1. The sample 2 is deposited or fastened, for example by bonding, on the optoacoustic transducer 1.

As described in relation with FIGS. 2 and 3, a pump beam 14 is generated, which comprises a train of ultra-short laser pulses, of variable repetition period F in the spectral domain of the gigahertz, and forming, in the spectral domain, an optical frequency comb having a free spectral interval ISL. An optomechanical system, for example with mirrors or polarizing components, directs the pump beam 14 towards the interface 3, for example by transmission from the surface 31 through the sample 2. In the example illustrated in FIG. 4, the pump beam 14 is incident on the surface 31 of the sample 2 and on the interface 3 with a normal angle of incidence.

A first pulse of the pump beam 14 is partly absorbed by the optoacoustic transducer 1 and generates a first acoustic front 21. Similarly, a second, respectively third, fourth, fifth pulse of the pump beam 14 is partly absorbed by the optoacoustic transducer 1 and generates a second, respectively third, fourth, fifth acoustic wave front 22, respectively 23, 24, 25. The acoustic wave fronts 21, respectively 22, 23, 24, 25, propagate from the interface 3 in the sample 2 at a speed that depends on the acoustic velocity V of the phonons in this sample 2. It is reminded that the light pulses of a same pulse train are temporally separated from each other by a time interval equal to 1/F, where F is the repetition period. If the sample 2 is homogenous, the acoustic wave fronts 21, 22, 23, 24, 25 are spatially separated from each other by a spatial period P that depends, on the one hand, on the repetition frequency F of the pulses of the pump beam 14 and, on the other hand, on the acoustic velocity V of the phonons in the sample 2. The pump beam 14 hence generates a spatially periodic grating of phonons 200. If the pulse train of the pump beam 14 includes a sufficient number of pulses, for example about two hundreds pulses, the phonon grating 200 is maintained and progressive in the sample 2.

Simultaneously, another part of the incident pulses, that is not absorbed by the optoacoustic transducer 1, is reflected by the interface 3 towards the sample 2 and forms a reflected beam 34. The probe beam 15 is herein consisted of ultra-short light pulses at the repetition frequency F. The probe beam 15 creates a plurality of beams 121, 122, 123, 124, 125 induced by Brillouin interaction on the phonon grating 200. The beams 121, 122, 123, 124, 125 interfere and form a scattering beam 120 by Brillouin scattering on the phonon grating 200. In the reverse direction of the incident probe beam 15, the reflection beam 34 and the scattering beam 120 are collected. When the acoustic path separating two successive fronts matches with the half-wavelength of the probe beam 15, the scattered beams 121, 122, 123, 124, 125 are in phase and produce constructive interferences. Hence, the interferences cumulate with each other and the Brillouin scattering signal is amplified in the return direction. A resonant Brillouin scattering effect is hence obtained.

Without being bound by theory, a first analysis of this physical phenomenon of resonant Brillouin scattering will now be described in detail. Coherent acoustic phonons are generated when an optical pulse of the pump beam 14 is absorbed by the optoacoustic transducer material 1, which is for example a metallic material. The superimposition of the coherent phonons causes a deformation front 121 that, during its propagation, locally disturb the optical index of the medium.

This modulation of the sample optical index allows detecting, by acousto-optical interaction, certain of the phonons generated. Indeed, for a weakly absorbent sample, a Brillouin interaction may be produced when the number of waves of the phonons is double than that of the probe beam 15. This condition is fulfilled when the acoustic frequency is equal to the Brillouin resonance frequency:

$$f_B = 2nV/\lambda$$

where n denotes the optical refractive index of the sample, V the acoustic velocity and λ the wavelength of the probe beam. Hence, when the index n is known, the measurement of the Brillouin resonance frequency leads to the mechanical properties (V) of the transparent sample.

According to the present disclosure, a probe beam consisted of a train of optical pulses, of repetition period 1/F adjustable in real time, is used to excite periodically coherent acoustic phonons so as to concentrate the acoustic excitation spectrum to the narrow band of the Brillouin interaction. Hence, when the repetition frequency F of the pulses of the pump beam 14 matches with the acoustic frequency of the Brillouin interaction, for a given optical wavelength of the probe beam 15, an extraordinary increase of the scattered signal is obtained, which allows separating, at the Brillouin resonance frequency, the portion of the detected signal corresponding to the reflection (on the surface 31 or on the interface 3, this reflection signal varying a little as a function of the repetition frequency F) of the portion of the detected signal that corresponds to the resonant Brillouin scattering on the grating of coherent acoustic phonons.

Another analysis of the physical phenomenon of resonant Brillouin scattering is explained in detail hereinafter. It is considered that a part of the probe beam 15 is reflected on an optical step index that accompanies the propagation of an acoustic wave front 121. Another part of the probe beam 15 is reflected by another optical step index that accompanies the propagation of another acoustic wave front 122, respectively 123, 124, 125. During the propagation of the acoustic wave front 121, the reflected beams produce on the photodetector 6 interferences whose spectral frequency is linked to the acoustic velocity of the acoustic wave front by the relation:

$$f_B = 2nV/\lambda \tag{I}$$

Hence, acoustic wave fronts 121, 122, 123, 125 that propagate in the medium 2 are generated periodically as a function of time. When the acoustic path separating two successive acoustic wave fronts is tuned to the optical wavelength of the probe light beam in the medium, an extraordinary increase of the reflected signal is then obtained.

In other words, the absorption of a pulse train of the pump beam 14 in the optoacoustic transducer medium 1 generates periodic acoustic fronts 21, 22, 23, 24, 25 in the transparent sample 2. When the repetition frequency F, of a few gigahertz, of the incident pulses is tuned to the frequency of the Brillouin interaction $f_B$, the probe beam 15 is efficiently refracted by Brillouin scattering.

The same pulse train may be used to generate the pump beam 14 and the probe beam 15, which contributes to make the assembly very simple, as illustrated in FIG. 2. The pump beam 14 creates the periodic excitation of the wave fronts and the probe beam 15 allows detecting interferences between the beams scattered on these wave fronts.

It is herein emphasized that the interferences are not temporally but, on the contrary, spectrally resolved, as a function of the variable repetition frequency F of the pump beam 14. The detection system implemented according to the present disclosure may hence be based on a very simple detection and avoids the use of a synchronous detection.

The acoustic spectrometry system of the present disclosure offers many advantages. Firstly, the possibility of adjusting easily the repetition frequency F of the pulse comb 14 allows tuning the generation of the coherent acoustic phonons with the Brillouin interaction of the sample to be analysed. Secondly, high power lasers are available nowadays, which make possible a spatially-resolved detection using a camera and hence a real-time full-field rather than point-by-point imagery.

In a non-spatially-resolved application, the detection system 6 includes a photodetector.

In another particular and advantageous embodiment, the detection system 6 includes a camera, for example of the CDD type, comprising a pixel array and an optical system forming an image of an area of the sample on the pixel array. The use of a light source system based on a high-intensity fibre laser at 1030 nm allows detecting a signal resulting from the Brillouin interaction on the camera pixel array. An acoustic spectrometry image as a function of the repetition frequency of the pulses is hence obtained. When the generation of coherent phonons is tuned to the Brillouin scattering frequency, the detected signal is strongly amplified. The scanning of the repetition frequency F hence allows revealing inhomogeneous Brillouin interaction frequencies within a heterogeneous sample such as a biological cell. This application of the resonantly stimulated Brillouin interaction to the real-time full-field imagery allows an extraordinary progress for the microscopy of mechanical properties.

Moreover, the optical system of the camera conjugates the image of an area of the sample with the detector array. Advantageously, the optical system is configured to obtain successive images of several planes of the sample in order to reconstruct a three-dimensional image of the structure of the sample. For example, the optical system comprises a microscope lens in confocal configuration, to form an image of a particular plane in a transparent sample, for example in micro-biology.

In the first embodiment described hereinabove, a single laser is used for generating the grating of coherent acoustic phonons and for detecting the resonant Brillouin interaction.

In a variant, two distinct laser pulse sources are used. A first source generates the pump beam 14 consisted of pulses at the variable repetition frequency F, to generate the periodic grating of coherent acoustic phonons in the sample. A second source generates the probe beam 15 to read the Brillouin scattering signal on this periodic grating of phonons. The second source may be a temporally continuous source or a source of light pulses, generating pulses at another repetition frequency.

Figure 5:
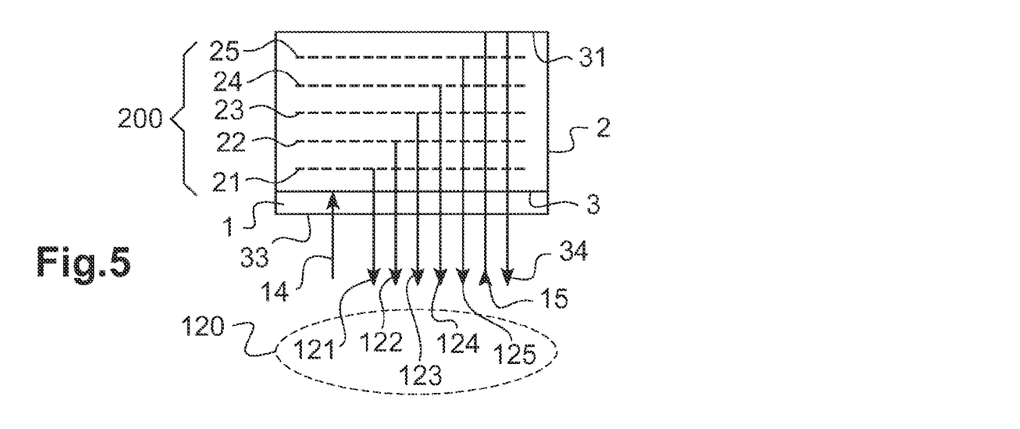
FIG. 5 illustrates a configuration for the resonant Brillouin scattering measurement according to a second embodiment of the invention.

In a second embodiment, illustrated in FIG. 5, the optoacoustic transducer 1 is consisted of a thin film absorbent at the wavelength of the pump beam 14 and transparent at the wavelength of the probe beam 15, which is herein different from the wavelength of the pump beam 14. The optoacoustic transducer 1 has an interface 3 with the sample 2 to be analysed. The pump beam 14 is directed towards a surface 33 of the optoacoustic transducer 1 so as to be absorbed in the optoacoustic transducer 1 before reaching the interface 3. The optoacoustic transducer 1 generates, by optoacoustic conversion, a grating of coherent acoustic phonons in the sample 2. Herein, the grating of coherent acoustic phonons propagates in the sample 2 in the same direction as the incident pump laser pulse. The probe beam 15 is directed towards the surface 33 of the optoacoustic transducer 1 so as to be transmitted in the sample via the interface 3. The probe beam 15 generates a scattering beam 120 by Brillouin scattering on the phonon grating. The advantage of this embodiment is to protect the sample from the pump beam 14.

Figure 6:
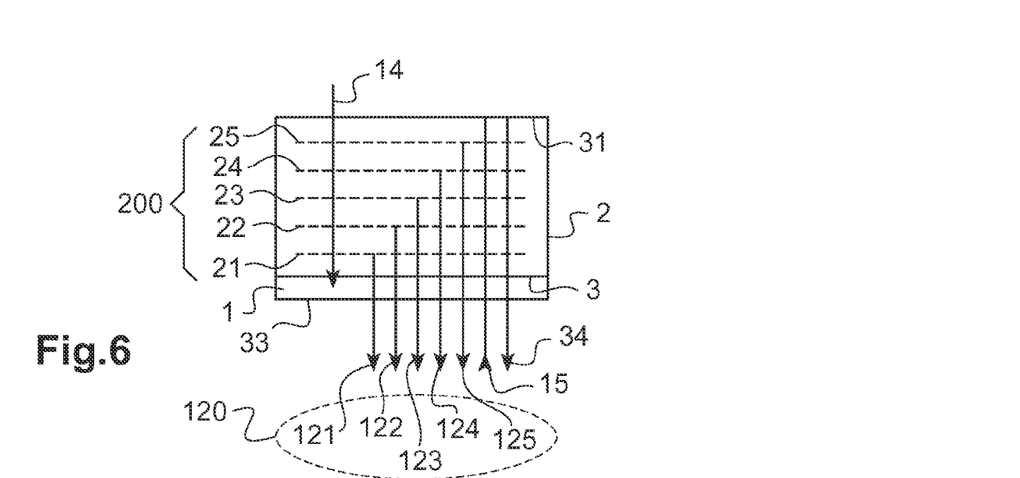
FIG. 6 illustrates a configuration for the resonant Brillouin scattering measurement according to a third embodiment of the invention.

In a third embodiment, illustrated in FIG. 6, the optoacoustic transducer 1 is consisted of a thin film absorbent at the wavelength of the pump beam 14 and transparent at the wavelength of the probe beam 15, which is herein different from the wavelength of the pump beam 14. The sample is herein transparent at the probe wavelength 15 and at the pump wavelength. The optoacoustic transducer 1 has an interface 3 with the sample 2 to be analysed. The pump beam 14 is directed towards a surface 31 of the sample, so as to be transmitted towards the interface 3 and absorbed in the optoacoustic transducer 1. The optoacoustic transducer 1 generates, by optoacoustic conversion, a grating of coherent acoustic phonons in the sample 2. Herein, the grating of coherent acoustic phonons propagates in the sample 2 in the opposite direction of the incident pump beam. The probe beam 15 is directed towards a surface 33 of the optoacoustic transducer 1 so as to be transmitted in the sample via the interface 3. The probe beam 15 generates a scattering beam 120 by Brillouin scattering on the phonon grating.

Figures 7, 8, 9:
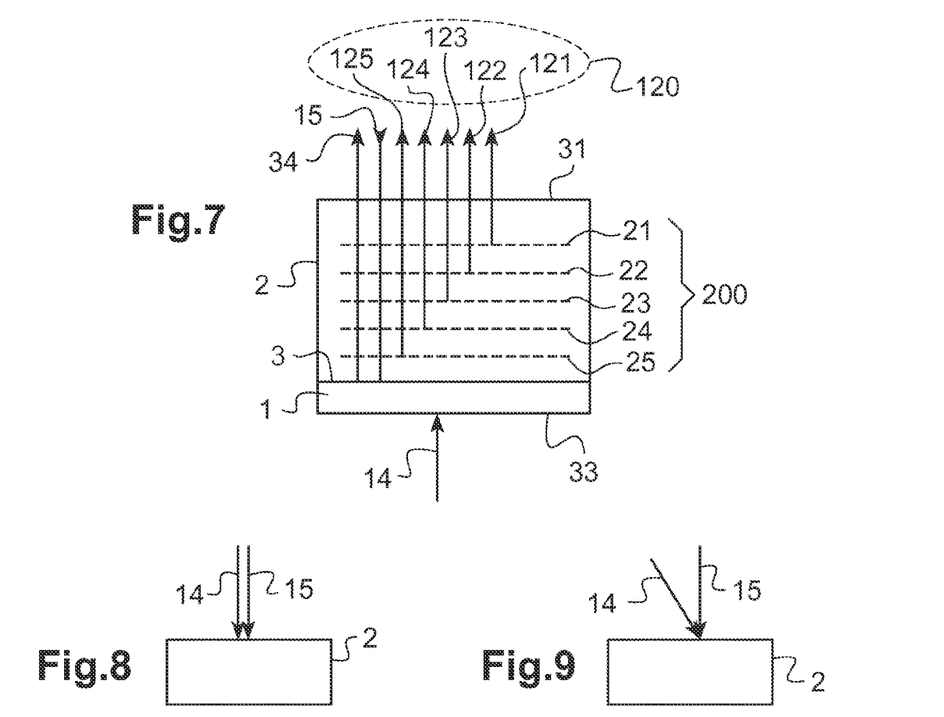
FIG. 7 illustrates a configuration for the resonant Brillouin scattering measurement according to a fourth embodiment of the invention.
FIG. 8 schematically shows a configuration of pump beam and probe beam in normal incidence on the sample.
FIG. 9 schematically shows a configuration of pump beam in oblique incidence and probe beam in normal incidence.

In a fourth embodiment, illustrated in FIG. 7, the optoacoustic transducer 1 is consisted of a thin film absorbent at the wavelength of the pump beam. The sample is herein transparent at the wavelength of the probe 15. The optoacoustic transducer 1 has an interface 3 with the sample 2 to be analysed. The pump beam 14 is directed towards a surface 33 of the optoacoustic transducer 1 so as to be absorbed in the optoacoustic transducer 1 before reaching the interface 3. The optoacoustic transducer 1 generates, by optoacoustic conversion, a grating of coherent acoustic phonons in the sample 2. Herein, the grating of coherent acoustic phonons propagates in the sample 2 in the same direction as the incident pump laser pulse. The probe beam 15 is directed towards a surface 31 of the sample. The probe beam 15 generates a scattering beam 120 by Brillouin scattering on the phonon grating. The advantage of this embodiment is also to protect the sample from the pump beam 14.

In the embodiments described in connexion with FIGS. 2, 4 to 7 and 8, the pump beam 14 that generates the phonon grating is incident on the optoacoustic transducer or on the interface with a normal angle of incidence and the probe beam 15 that forms interferences on this phonon grating is incident on the surface 31 of the sample 2 and on the interface 3 with a normal angle of incidence.

Other angles of incidence are considered herein without departing from the scope of the present disclosure.

Figure 10:
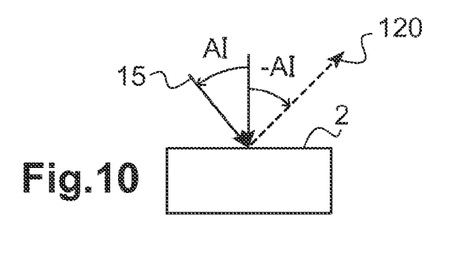
FIG. 10 schematically shows a configuration of pump beam in normal incidence and probe beam in oblique incidence.
Figure 11:
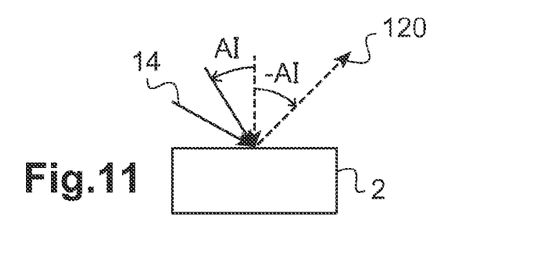
FIG. 11 schematically shows a configuration of pump beam in incidence and probe beam in oblique incidence on the sample.

Hence, in FIG. 9, the pump beam 14 is incident on the sample 2 with an oblique angle of incidence and the probe beam 15 is incident on the sample 2 with a normal angle of incidence. In FIG. 10, the pump beam 14 is incident on the sample 2 with a normal angle of incidence and the probe beam 15 is incident on the sample 2 with an oblique angle of incidence. In FIG. 11, the pump beam 14 is incident on the sample 2 with an oblique angle of incidence and the probe beam 15 is incident on the sample 2 with another oblique angle of incidence. The angle of incidence of the probe beam 15 on the sample is denoted A.I. The scattered beam 120 is measured in the direction forming an opposite angle −A.I. with the normal to the sample. The one skilled in the art will easily adapt these different angles of incidence to the embodiments described in relation with FIGS. 4 to 7.

The pitch P of the phonon grating varies in accordance with a known function of the angle of incidence of the excitation beam. Likewise, the Brillouin scattering frequency and the appearance of interferences vary in a known manner as a function of the angle of incidence of the probe beam on the sample.

Figure 12:
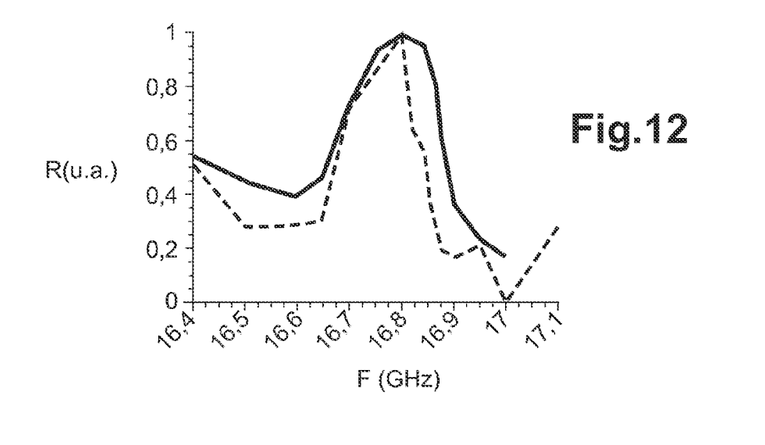
FIG. 12 shows an example of acoustic resonance spectrometry measurements.

In FIG. 12 is shown an example of surface reflectivity measurements on two different samples of silica as a function of the repetition frequency F of the laser pulses, in a spectral range comprised between 16.4 GHz and 17.1 GHz. The optoacoustic transducer is herein a metal film having a planar interface with the sample. The repetition frequency is herein incrementally modified by steps of 20 MHz. The intensity of the detected signal is shown in FIG. 12. The significant increase of the detected signal reveals the expected Brillouin interaction for the silica, at the wavelength of the probe beam of 1030 nm, when the repetition frequency F of the pump beam pulses is of about 16.8 GHz. This repetition frequency matches with the known values for the optical index and the acoustic velocity of the silica.

The system and method object of the present disclosure hence allow measuring the elastic properties of transparent mediums, liquid or solid, possibly of biological nature. These mechanical property measurements are performed in a non-destructive way and without contact, which is a noticeable advantage. The making of an acoustic spectrometry system combined with a full-field imaging system allows mapping the Brillouin frequency of a sample within a few milliseconds and with a spatial resolution of the order of one micrometre.

A signal processing system allows deducing from these Brillouin scattering measurements different properties associated with different applications.

The following applications are in particular contemplated.

The Brillouin scattering allows measuring the velocity of the scattering acoustic wave, which depends on the compressibility of the medium. The acoustic velocity as well as the optical refractive index n being sensitive to the residual mechanical constraints, the system and method object of the present disclosure may hence allow detecting these mechanical constraints.

The optoacoustic transducer 1 generates coherent acoustic phonons and transmits them towards the sample to be analysed. Now, the amplitude of the coherent acoustic phonons present in the sample depends on the mechanical contact at the interface between the metal of the optoacoustic transducer 1 and the transparent thin layer of the sample to be analysed. The adhesion properties may hence be characterized, in particular for assemblies in the field of microelectronics.

These analyses find applications in different technological fields. In photonics, the Brillouin scattering measurements may be analysed to deduce therefrom a measurement of the elasticity and/or the imagery of adhesion defects between one or several transparent thin layers, used for example in optical systems or components, for example in eyewear. In electronics, the Brillouin scattering measurements may be analysed to deduce therefrom a measurement of elasticity of transparent thin films used for example in the mobile phones, or for the control of adhesion of the transparent thin electronic components. In the mechanical industry, it may be deduced from the Brillouin measurements, a measurement of the elasticity and adhesion of hardening thin layers deposited on the cutting tools used in machining, in particular high-speed machining (cutting tool coatings, for example made of carbide). In cellular biology, or in medical biology applications, acoustic waves of frequencies much higher than those used in conventional acoustic microscopy may be optically generated and detected by Brillouin interaction in the cellular medium. In particular, it has been shown that the signals relating to the core and respectively to the vacuole of vegetal cells are substantially different. The application of the imaging system according to the present disclosure allows producing maps of the compressibility and adhesion of individual cells, or of a population of cells coming for example from histological cuts. The different compressibility of the healthy and tumoral cells may allow the identification thereof for biological and/or diagnostic analyses.

The invention claimed is:

1. An acoustic resonance spectrometry system for analysing a sample (2), the system including:
   an optoacoustic transduction means (1) having an interface (3) in contact with the sample (2) to be analysed,
   an optical pump-probe device (4) adapted to generate a pump beam (14) and a probe beam (15),
   the pump beam (14) being consisted by a series of ultrashort pump light pulses having a repetition frequency (F) located in a spectral domain comprised between several hundreds of megahertz and several tens of gigahertz, optomechanical means for directing the pump beam (14) towards the optoacoustic transduction means (1) for generating a periodic grating of coherent acoustic phonons (200) in the sample (2), the periodic grating of phonons (200) having a pitch (P) determined as a function a ratio (V/F) between the repetition frequency (F) of the pump beam (14) and an acoustic velocity (V) of the coherent acoustic phonons (200) in the sample (2);
   other optomechanical means for directing the probe beam (15) towards the sample (2), so as to form a scattering beam (120) of the probe beam (15) on the periodic grating of coherent acoustic phonons (200),
   a frequency variation device (5) adapted to vary the repetition frequency (F) of the pump beam (14) in a spectral range of said spectral domain, so as to vary the pitch (P) of the grating of coherent acoustic phonons (200) in the sample (5), and
   a photo-detection system (6) configured to receive the scattering beam (120) and to measure a scattering signal as a function of the repetition frequency in said spectral range.

2. The system according to claim 1, wherein the optical pump-probe device (4) comprises a laser (40) configured to emit a monochromatic continuous laser beam (140), a variable frequency microwave generator configured to generate a control signal at said repetition frequency and a plurality of electro-optical modulators (41, 42, 43, 44) configured to receive the control signal and to modulate the monochromatic continuous laser beam in amplitude and in phase at said repetition frequency and a compressor (46) configured to receive the laser beam modulated in amplitude and in phase at said repetition frequency and to generate the pump beam (14), the pump beam (14) having a spectral distribution comprising a plurality of discrete wavelengths separated by a free spectral interval determined by the repetition frequency.

3. The system according to claim 2, wherein the probe beam is temporally continuous.

4. The system according to claim 2, wherein the probe beam is consisted by another series of ultra-short light pulses.

5. The system according to claim 2, wherein the pump beam having a pump wavelength, the probe beam having a probe wavelength, the probe wavelength is different from the pump wavelength.

6. The system according to claim 2, wherein the pump beam having a pump wavelength, the probe beam having a probe wavelength, the probe wavelength is equal to the pump wavelength.

7. The system according to claim 1 wherein the probe beam (15) is temporally continuous.

8. The system according to claim 7, wherein the pump beam having a pump wavelength, the probe beam having a probe wavelength, the probe wavelength is different from the pump wavelength.

9. The system according to claim 7, wherein the pump beam having a pump wavelength, the probe beam having a probe wavelength, the probe wavelength is equal to the pump wavelength.

10. The system according to claim 1, wherein the probe beam (15) is consisted by another series of ultra-short light pulses.

11. The system according to claim 10, wherein the probe beam (15) is consisted of a portion of the pump beam (14).

12. The system according to claim 10, wherein the pump beam having a pump wavelength, the probe beam having a probe wavelength, the probe wavelength is different from the pump wavelength.

13. The system according to claim 10, wherein the pump beam having a pump wavelength, the probe beam having a probe wavelength, the probe wavelength is equal to the pump wavelength.

14. The system according to claim 1, wherein the pump beam (14) having a pump wavelength, the probe beam (15) having a probe wavelength, the probe wavelength is different from the pump wavelength.

15. The system according to claim 14, wherein the probe beam is consisted of a portion of the pump beam.

16. The system according to claim 1, wherein the pump beam (14) having a pump wavelength, the probe beam (15) having a probe wavelength, the probe wavelength is equal to the pump wavelength.

17. The system according to claim 16, wherein the probe beam is consisted of a portion of the pump beam.

18. The system according to claim 1, wherein the pump beam (14) and the probe beam (15) are in normal incidence on the sample, or wherein the pump beam (14) is in normal incidence on the sample and the probe beam (15) in oblique incidence on the sample, or wherein the pump beam (14) is in oblique incidence on the sample and the probe beam (15) in normal incidence on the sample, or wherein the pump beam (14) is in oblique incidence on the sample and the probe beam (15) has another oblique incidence on the sample.

19. The system according to claim 1, wherein the probe beam (15) is configured to illuminate an area of the sample (2) and wherein the photo-detection system (6) includes a two dimensionally-resolved image detector and an optical system configured to form an image of said sample area on the image detector.

20. An acoustic resonance spectrometry method, the method comprising the following steps:
generating a pump beam (14) consisted by a series of ultra-short pump light pulses having a repetition frequency (F) located in a spectral domain comprised between several hundreds of megahertz and several tens of gigahertz,
the pump beam (14) being incident on an optoacoustic transduction means (1) having an interface (3) with a sample (2) to be analysed, so as to generate a periodic grating of coherent acoustic phonons (200) in the sample (2), the periodic grating of phonons (200) having a pitch (P) determined as a function of a ratio (V/F) between the repetition frequency (F) of the pump beam (14) and an acoustic velocity (V) of the coherent acoustic phonons (200) in the sample (2),
generating a probe beam (15), the probe beam (15) being directed towards the sample (2) so as to form a scattering beam (120) by scattering of the probe beam (15) on the periodic grating of coherent acoustic phonons (200),
varying the repetition frequency (F) of the pump beam (14) in a spectral range so as to vary the pitch (P) of the periodic grating of coherent acoustic phonons (200) in the sample (5),
photo-detecting the scattering beam (120) as a function of the repetition frequency (F) in said spectral range, and
measuring a scattering signal as a function of the repetition frequency (F) in said spectral range.

* * * * *